(12) United States Patent
Liu et al.

(10) Patent No.: US 11,841,355 B2
(45) Date of Patent: Dec. 12, 2023

(54) INTELLIGENT QUANTITATIVE MICROSCOPIC IDENTIFICATION SYSTEM AND INTELLIGENT IDENTIFICATION METHOD FOR WHOLE ROCK POLISHED SECTIONS

(71) Applicant: YANGTZE UNIVERSITY, Jingzhou (CN)

(72) Inventors: Yan Liu, Hubei (CN); Feilong Wang, Tianjin (CN); Zhigang Wen, Hubei (CN); Qingyong Luo, Beijing (CN); Lei Lan, Beijing (CN); Shuchun Yang, Beijing (CN); Yongjing Tian, Hubei (CN); Yaohui Xu, Hubei (CN); Guangyou Zhu, Beijing (CN); Xiangchun Chang, Shandong (CN); Meijun Li, Beijing (CN)

(73) Assignee: YANGTZE UNIVERSITY, Jingzhou (CN)

( * ) Notice: Subject to any disclaimer, the term of this patent is extended or adjusted under 35 U.S.C. 154(b) by 172 days.

(21) Appl. No.: 17/515,880

(22) Filed: Nov. 1, 2021

(65) Prior Publication Data
US 2022/0146487 A1   May 12, 2022

(30) Foreign Application Priority Data

Nov. 6, 2020 (CN) .......................... 202011225530.8
Mar. 25, 2021 (CN) .......................... 202110317048.5

(51) Int. Cl.
*G01N 33/24* (2006.01)
*G01N 1/32* (2006.01)
(Continued)

(52) U.S. Cl.
CPC ............. *G01N 33/24* (2013.01); *G01N 1/286* (2013.01); *G01N 1/32* (2013.01); *G01N 21/01* (2013.01);
(Continued)

(58) Field of Classification Search
CPC .......... G01N 33/24; G01N 1/286; G01N 1/32; G01N 21/01; G01N 21/8851;
(Continued)

(56) References Cited

U.S. PATENT DOCUMENTS 5,196,716 A * 3/1993 Moriya .............. G01N 21/9505
250/559.46
2004/0237331 A1* 12/2004 Sarfaty ................. B24B 19/226
34/218

FOREIGN PATENT DOCUMENTS

CN         1635360 A      7/2005
CN    203132900 U  *   8/2013  ............. G01N 21/84
(Continued)

OTHER PUBLICATIONS

Wenqi Song, Mechanical manufacturing process automation, Apr. 1, 1985, Yunnan People's Publishing House, China.
(Continued)

*Primary Examiner* — Jamil Ahmed
(74) *Attorney, Agent, or Firm* — Dragon Sun Law Firm, PC; Nathaniel Perkins

(57) ABSTRACT

The invention provides an intelligent quantitative microscopic identification system for whole rock polished sections, which can greatly improve the collection efficiency of whole rock polished sections by adopting a microscopic collecting apparatus. In a preferable technical solution, the microscopic collecting apparatus is combined with the production line for the automatic preparation of whole rock polished sections to form an integrated system, which real-
(Continued)

izes an automatic solution from preparation to collection, therefore further improves the production and collection efficiency of whole rock polished sections, and which can cope with production, image collection and automatic scanning and splicing of mass whole rock polished sections, so it greatly improves the collection efficiency of the microscopic images of organic components for whole rock polished sections. People can collect 500 to 1000 sample pieces of whole rock polished sections in 12 hours by adopting the solution of the invention.

13 Claims, 13 Drawing Sheets
(4 of 13 Drawing Sheet(s) Filed in Color)

(51) Int. Cl.
  *G01N 21/88* (2006.01)
  *G01N 21/01* (2006.01)
  *G01N 1/28* (2006.01)
  *G02B 21/06* (2006.01)
  *G02B 21/26* (2006.01)
  *G02B 21/36* (2006.01)
(52) U.S. Cl.
  CPC ......... *G01N 21/8851* (2013.01); *G02B 21/06* (2013.01); *G02B 21/26* (2013.01); *G02B 21/365* (2013.01); *G01N 2001/2866* (2013.01); *G01N 2021/8887* (2013.01)
(58) Field of Classification Search
  CPC ... G01N 2001/2866; G01N 2021/8887; G02B 21/06; G02B 21/26; G02B 21/365
  See application file for complete search history.

(56) References Cited

FOREIGN PATENT DOCUMENTS

| | | |
|---|---|---|
| CN | 203132900 U | 8/2013 |
| CN | 103492851 A | 1/2014 |
| CN | 104330294 A | 2/2015 |
| CN | 104977204 A | 10/2015 |
| CN | 205880353 U | 1/2017 |
| WO | 2010148435 A1 | 12/2010 |

OTHER PUBLICATIONS

Kuanming He, Coal Chemistry, May 1, 2010, Metallurgical Industry Press, China.
Xianghe Xu et al., Electronic precision mechanical design, Oct. 1, 2000, Southeast University Press, China.

* cited by examiner

INTELLIGENT QUANTITATIVE MICROSCOPIC IDENTIFICATION SYSTEM AND INTELLIGENT IDENTIFICATION METHOD FOR WHOLE ROCK POLISHED SECTIONS

CROSS-REFERENCE TO RELATED APPLICATIONS

This application claims priorities from the Chinese patent application 202011225530.8 filed Nov. 6, 2020, and from Chinese patent application 2021103170485, filed Mar. 25, 2021, the content of which are incorporated herein in the entirety by reference.

TECHNICAL FIELD

The invention relates to the technical field of geological exploration to petroleum and natural gas, in particular to an intelligent quantitative microscopic identification system and intelligent identification method for whole rock polished sections.

BACKGROUND ART

The organic microscopic component is the hydrocarbon generation part in the source rock, the content and composition difference of which has an important influence on the properties and hydrocarbon generation characteristics of coal and source rocks. In the early stage, people quantified the organic microscopic component by means of coal petrography, making an estimate by visual estimation adopting single-view analysis. Among them, the method most widely used is the method adopting a points-counting estimation to the content of each organic microscopic component provided by the International Coal and Organic Petrology Committee in 1971. Based on the identification to microscopic components, this method determines the percentage of various components in the whole rock volume. By means of counting the points to "cover a surface by points" and "forming a solid by surfaces", people calculate the content of each organic microscopic component after counting more than 500 effective points. This method is extremely time-consuming and inefficient, and greatly affected by human experience. The data results are non-reproducible, and a lot of useful geological information is lost, which limits the application scope of the organic petrology method. The Chinese patent document CN110426350A provides a method for quantifying the composition of microscopic components in rocks. The patent document CN111160064A of the Coal Science and Technology Research Institute Co., Ltd. provides an identification method for coal and rock components adopting the processing and the zone-division of the frequency curve of gray-scale-accumulation, but due to the point edges caused by the single-color division it has great shortcomings. A method for quickly polishing sections according to the Chinese patent document CN 104515698A greatly improves the efficiency of making whole rock polished sections, but still has low efficiency in preparation and collection of mass whole rock polished sections, which limits rapid development of geological exploration.

SUMMARY OF THE INVENTION

The technical problem to be solved by the invention is to provide an intelligent quantitative microscopic identification system and intelligent identification method for whole rock polished sections, which can greatly improve the preparation efficiency of whole rock polished sections and the collection speed, splicing and identification efficiency of whole rock polished sections.

The technical solution adopted by the present invention is to solve the technical problem that: an intelligent quantitative microscopic identification system for whole rock polished sections, comprising a microscope, a mage collection apparatus is provided with the eyepiece of the microscope, a light source having multiple groups of different illumination modes is provided with the objective lens of the microscope and a X-Y stepping working stand is arranged under the objective lens of the microscope;

wherein the X-Y stepping work stand is used to fix a rock sample and drive the rock sample to move step-by-step along the X and Y axes; or the X-Y stepping work stand is used to fix a rock sample and drive the objective lens of the microscope move step-by-step along the X and Y axis;

the image collection apparatus is electrically connected to the computer.

As provided by the preferable solution, the system further including a glue-injecting apparatus, a vibrated delivery slideway, an UV solidifying tunnel and a plurality of grinding working sections;

the grinding working sections includes a coarse grinding work section, a precision grinding work section and a polishing work section;

the glue-injecting apparatus, the vibrated delivery slideway, the UV solidifying tunnel, the coarse grinding work section, the precision grinding work section and the polishing work section are arranged in sequence along the upstream and downstream of a conveyor belt;

the glue-injecting apparatus is used to inject UV glue into a sample vessel;

the vibrated delivery slideway is used to spread the sieved rock samples on the surface of the UV glue;

the UV solidifying tunnel is used to solidify the UV glue in the sample vessel;

the grinding section is provided with the coarse grinding work section, the precision grinding work section and the polishing work section, which are used for grinding and polishing the surface of the solidified rock sample to obtain whole rock polished sections.

As provided by the preferable solution, the sample vessel is provided with a forming ring, which has a transparent ring structure, and the bottom of which touches the inner bottom of the sample vessel to form sealing;

a draft angle a is arranged inside the forming ring.

As provided by the preferable solution, the downstream of the UV solidifying tunnel is also provided with a sampling work stand, one side of downstream of which is provided with a bar code printer;

one side of the X-Y stepping work stand is also provided with a bar code scanner used for scanning the barcode on the rock sample;

a buffer stocker is provided in the upstream of the barcode scanner.

As provided by the preferable solution, the coarse grinding work section is configured to arrange a lower grinding apparatus opposite to an upper grinding apparatus, and a lifting clamping head between the lower grinding apparatus and the upper grinding apparatus, and connect the lifting clamping head to a lifting frame, and the lifting frame to a lifting motor through a screw nut mechanism, the lifting motor drives the lifting frame up and down, so that the lifting clamping head moves backwards and forwards between the lower grinding apparatus and the upper grinding apparatus, the lower grinding apparatus and the upper grinding apparatus have a surface parallelism between them that meets the design requirements.

As provided by the preferable solution, the precision grinding work section and the polishing work section are configured to arrange the lifting clamping head below the upper grinding apparatus, and connect the lifting clamping head to the lifting frame, and the lifting frame to the lifting motor through the screw nut mechanism, the lifting motor drives the lifting frame up and down, so that the lifting clamping head moves backwards and forwards with respect to the upper grinding apparatus.

As provided by the preferable solution, one side of the coarse grinding work section, the precision grinding work section and the polishing work section is provided with a plurality of laterally-pushing cylinders, the laterally-pushing cylinder is provided with a clamping mechanical claw used to push the solidified rock sample into the coarse grinding work section, the precision grinding work section and the polishing work section, or pick out the solidified rock sample from the coarse grinding work section, the precision grinding work section or the polishing work section.

As provided by the preferable solution, the upstream of the coarse grinding work section, the precision grinding work section or the polishing work section is provided with detection sensors respectively, which are used to detect the solidified rock sample passing by them, so as to push the solidified rock sample into the corresponding work station.

As provided by the preferable solution, the feeding side of the X-Y stepping work stand is provided with a bar code scanner used to scan the barcode on the rock sample.

As provided by the preferable solution, the X-Y stepping work stand is provided with a X-direction servo motor and a Y-direction servo motor, which are used to drive the work stand to move a set distance in the X-direction or the Y-direction.

The invention provides an intelligent quantitative microscopic identification system for whole rock polished sections, which can greatly improve the collection efficiency of whole rock polished sections by adopting a microscopic collecting apparatus. In a preferable technical solution, the microscopic collecting apparatus is combined with the production line for the automatic preparation of whole rock polished sections to form an integrated system, which realizes an automatic solution from preparation to collection, therefore further improves the production and collection efficiency of whole rock polished sections, and which can cope with production, image collection and automatic scanning and splicing of mass whole rock polished sections, so it greatly improves the collection efficiency of the microscopic images of organic components for whole rock polished sections. People can collect 500 to 1000 sample pieces of whole rock polished sections in 12 hours by adopting the solution of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

We will further describe the invention below in combination with the figures and embodiments.

Wherein, 1-X-Y stepping work stand; 101—X-direction servo motor; 102—Y-direction servo motor; 2—rock sample; 3—first light source; 4—second light source; 5—image collection apparatus; 6—computer; 7—microscope; 8—vessel-supplying tower; 81—opening; 9—sample vessel; 91—shallow slot; 10—forming ring; 11—conveyer belt; 12—glue-injecting apparatus; 13—classifying sieve; 14—waste slideway; 15—vibrated delivery slideway; 16—delivery sensor; 17—UV solidifying tunnel; 18—solidified rock sample; 19—first detection sensor; 20—coarse grinding work section; 21—monitor sieve; 22—second detection sensor; 23—precision grinding work section; 24—third detection sensor; 25—polishing work section; 26—laterally-pushing cylinder; 261—clamping mechanical claw; 27—lower grinding apparatus; 28—lifting motor; 29—lifting frame; 30—upper grinding apparatus; 31—lifting clamping head; 32—camera; 33—bar code scanner; 34—sampling work stand; 35—bar code printer; 36—buffer stocker; 37—objective lens; 38—screw nut mechanism; a—draft angle.

DETAILED DESCRIPTION OF THE PREFERRED EMBODIMENTS

Example 1

Figure 1:
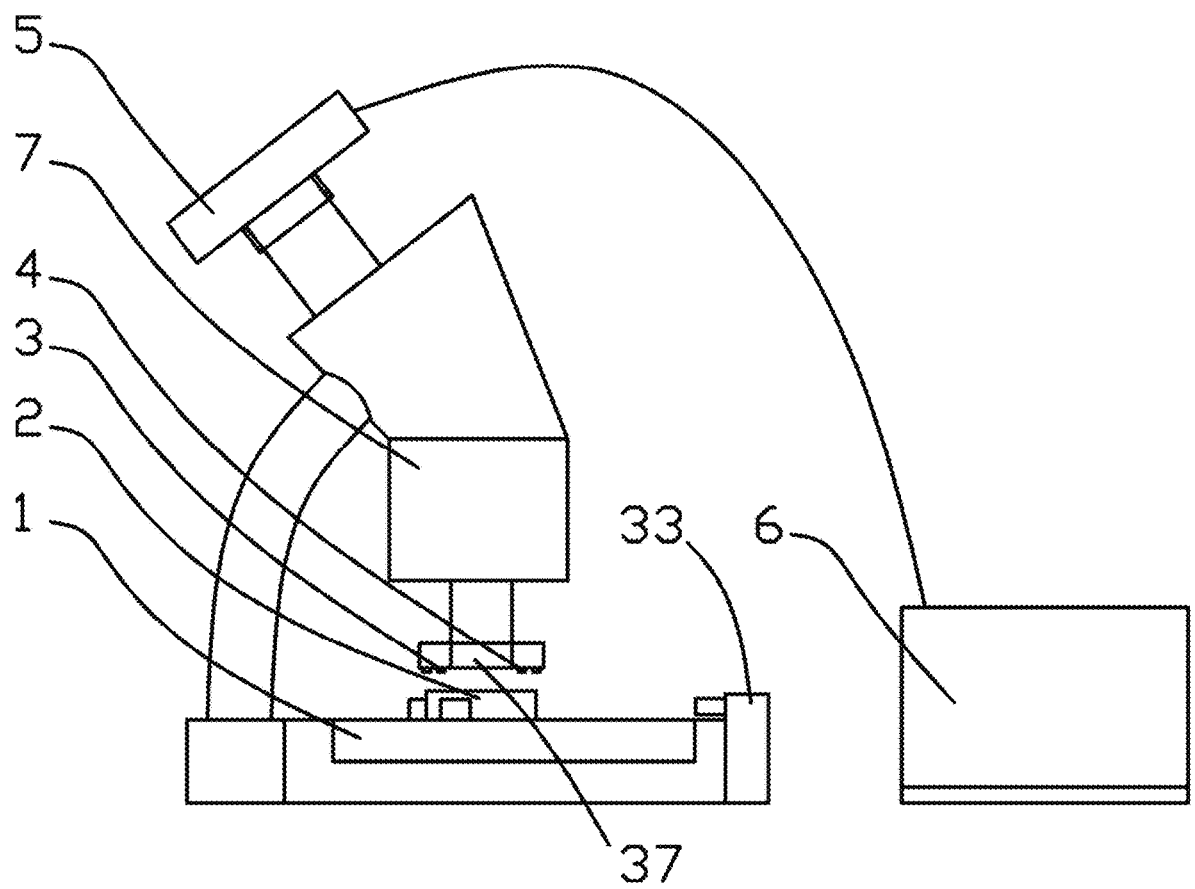
FIG. 1 is a schematic diagram of the microscopic collecting apparatus in the invention.

As shown in FIG. 1, the intelligent quantitative microscopic identification system for whole rock polished sections includes the microscope 7, the eyepiece of which is equipped with the image collection apparatus 5, and the objective lens of which is equipped with the light sources having multiple groups of different illumination modes, such as the first light source 3 and the second light source 4, and the X-Y stepping work stand 1 is arranged below the objective lens of the microscope 7.

The X-Y stepping work stand 1 is used to fix the rock sample 2 and drive the rock sample 2 to move step-by-step along the X and Y axes; or the X-Y stepping work stand 1 is used to fix the rock sample 2 and drive the objective lens of the microscope 7 to move step-by-step along the X and Y axis.

The image collection apparatus 5 is electrically connected to the computer 6. Adopting this structure, we realized automatically collecting the images of the rock sample 2 by means of automatic scanning and digital collection, which greatly improves the collection efficiency of whole rock polished sections, thereby speeding up the feedback of the survey results.

Figure 2:
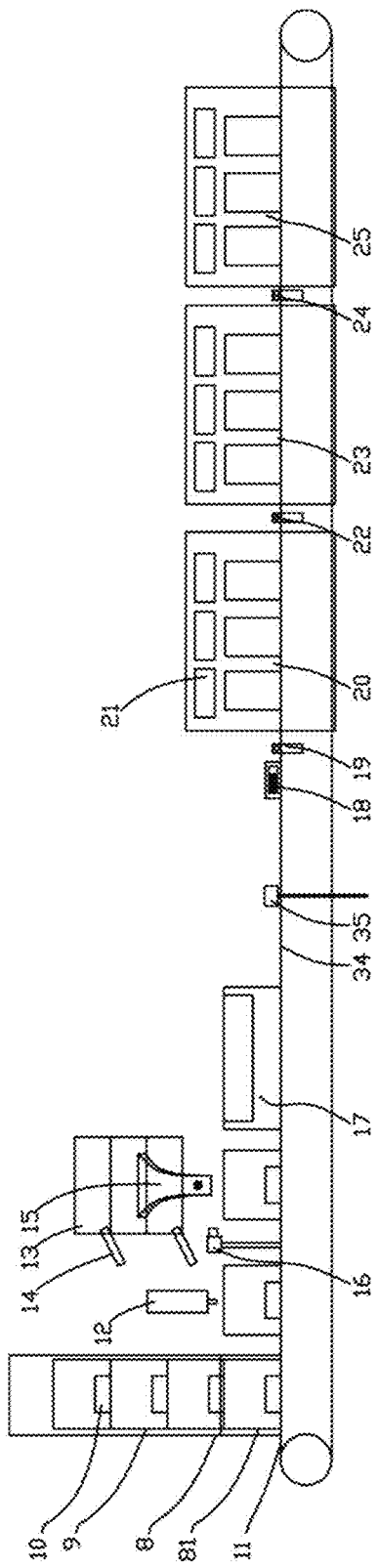
FIG. 2 is a schematic diagram of the prepared rock sample in the invention.

The preferable solution shown in FIG. 2 further includes the glue-injecting apparatus 12, the vibrated delivery slideway 15, the UV solidifying tunnel 17 and a plurality of grinding working sections.

The grinding working sections includes the coarse grinding work section 20, the precision grinding work section 23 and the polishing work section 25.

The glue-injecting apparatus 12, the vibrated delivery slideway 15, the UV solidifying tunnel 17, the coarse grinding work section 20, the precision grinding work section 23 and the polishing work section 25 are arranged in sequence along the upstream and downstream of the conveyor belt 11;

The glue-injecting apparatus 12 is used to inject UV glue into the sample vessel 9. Preferably, the vibrated delivery slideway 15 is connected to the classifying sieve 13, the upper level of which has 2-3 mm meshes, and the lower level of which has 0.5 mm meshes, and the vibrated delivery slideway 15 is connected to the lower level of the classifying sieve 13 to obtain the rock sample granules with particle size of 0.5-2 mm.

The vibrated delivery slideway 15 is used to spread the sieved rock samples on the surface of the UV glue.

The UV solidifying tunnel 17 is used to solidify the UV glue in the sample vessel 9.

Figure 3:
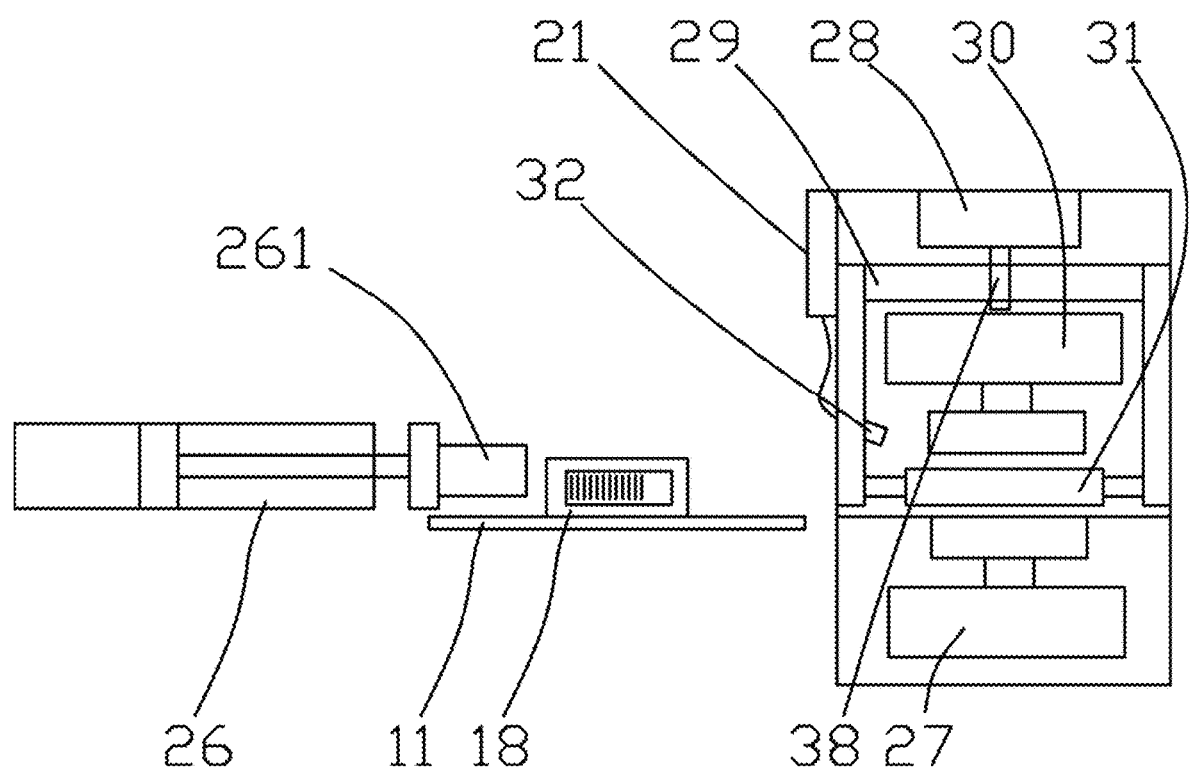
FIG. 3 is a schematic diagram of the coarse grinding work section in the invention.
Figure 4:
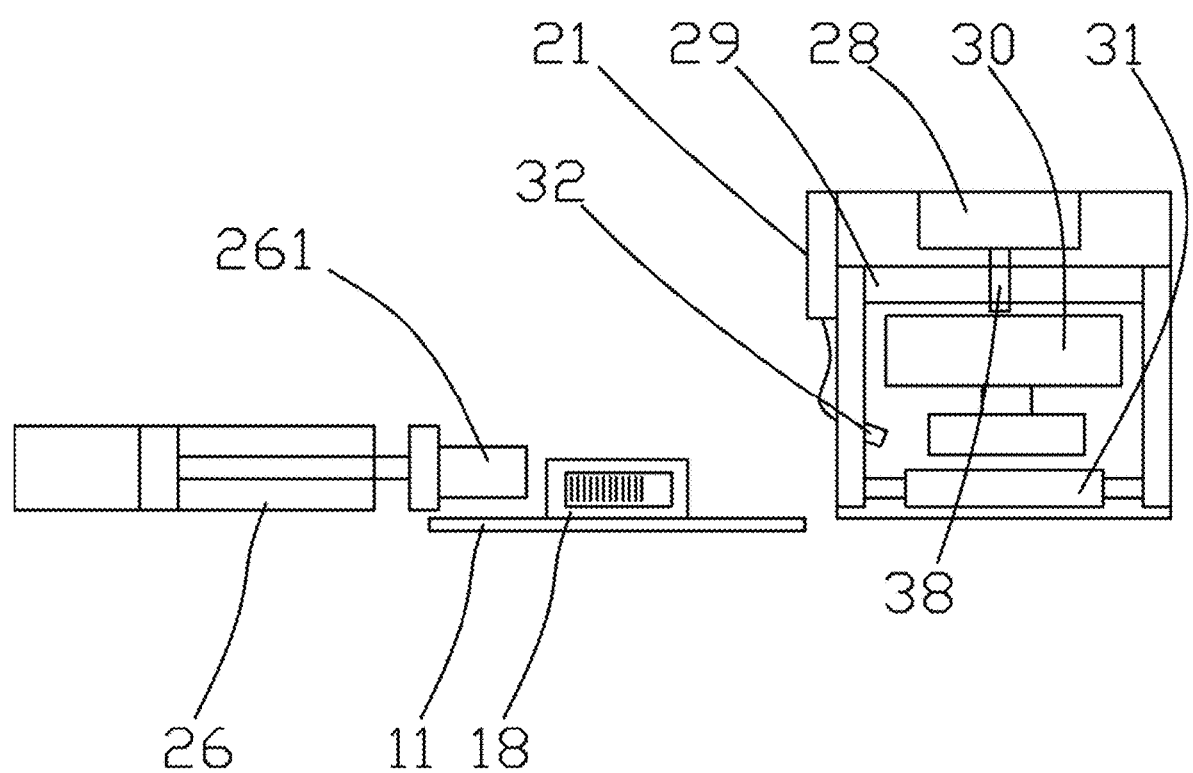
FIG. 4 is a schematic diagram of the precision grinding work section in the invention.

The grinding section is provided with the coarse grinding work section 20, the precision grinding work section 23 and the polishing work section 25, which are used for grinding and polishing the surface of the solidified rock sample to obtain whole rock polished sections. The upstream and downstream in this example refer to the movement direction of the sample vessel 9 or the solidified rock sample 18 on the conveyor belt 11. The detection sensors, such as the first detection sensor 19, the second detection sensor 22, and the third detection sensor 24 are arranged in the upstream of the coarse grinding work section 20, the precision grinding work section 23 and the polishing work section 25. Preferably, the detection sensors is made of a photoelectric sensor to detect the solidified rock sample 18 passing by them, so as to facilitate to push the solidified rock sample 18 into the corresponding working section by the laterally-pushing cylinder 26 according to the position of the solidified rock sample 18 as shown in FIGS. 3 and 4. Preferably, each working section is provided with a plurality of work stations, so as to polish a plurality of solidified rock samples 18 at the same time. Preferably, the number of the arranged work stations should fulfil the processing capacity of the coarse grinding work section 20, the precision grinding work section 23 and the polishing work section 25 being higher than that of other working sections, so as to avoid obstruction.

Figure 13:
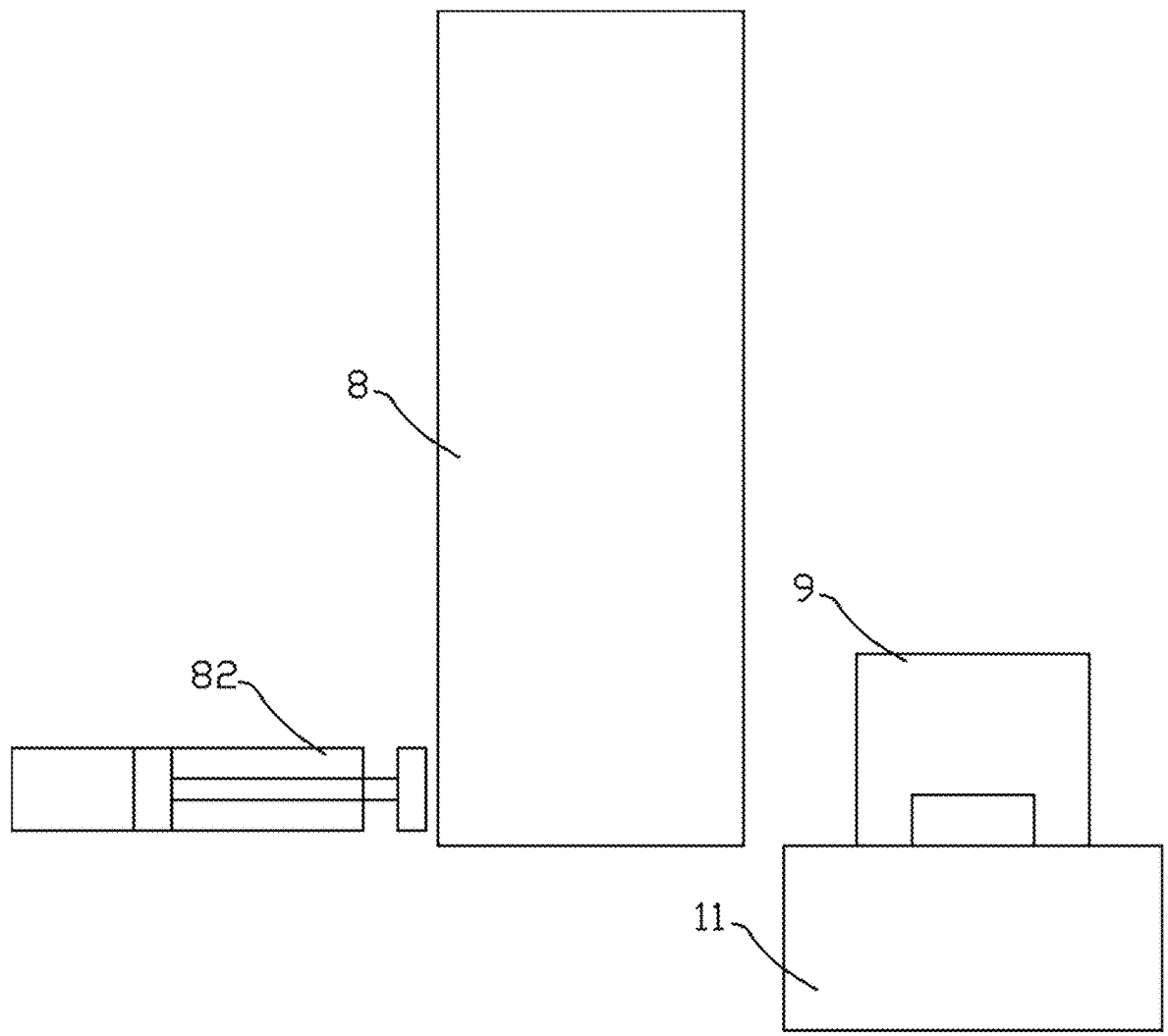
FIG. 13 is a schematic diagram of an upwardly-pushing apparatus provided on the bottom of a vessel-supplying tower in the invention.

As provided by the preferable solution shown in FIG. 2, in the upstream of the glue-injecting apparatus 12, one side of the conveyor belt 11 is provided with the vessel-supplying tower 8, the bottom of which is provided with the opening 81, and inside which the sample vessels 9 are stacked, as shown in FIG. 13, a upwardly-pushing apparatus 82 is provided on the bottom of the vessel-supplying tower 8, so as to push one of the stacked sample vessels 9 onto the conveyor belt 11. The upwardly-pushing apparatus 82 adopts the same cylinder-driven structure as that of the laterally-pushing cylinder 26.

Figure 6:
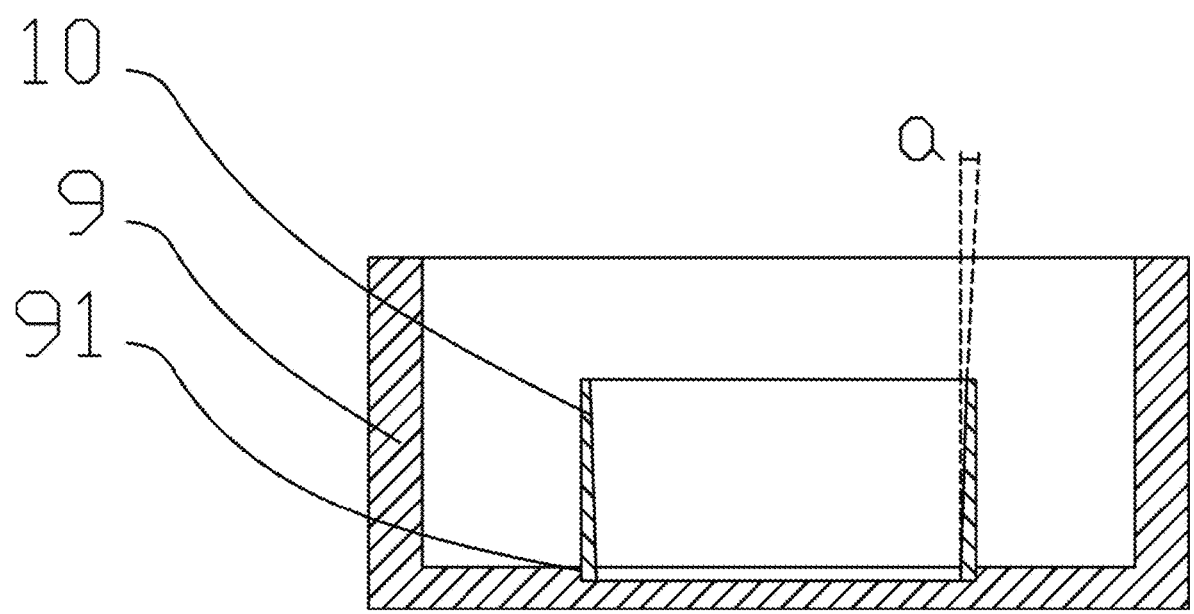
FIG. 6 is a schematic diagram of the sample vessel in the invention

As provided by the preferable solution shown in FIG. 6, the sample vessel is provided with the forming ring 10, which has a ring structure, preferably is made from transparent material, and the bottom of which touches the inner bottom of the sample vessel to form sealing. In this example, the shallow slot is provided at the bottom of the sample vessel 9, which is precisely processed by CNC, the forming ring 10 is made from glass, and the inner wall of the sample vessel 9 is sprayed with a release agent. The draft angle a is arranged inside the forming ring 10, being 5° in this example, that is, the inner ring of the forming ring 10 has a smaller diameter at the bottom and a larger diameter at the top, which helps to take out the solidified rock sample 18.

As provided by the preferable solution shown in FIG. 2, the downstream of the UV solidifying tunnel 17 is also provided with the sampling work stand 34, one side of downstream of which is provided with the bar code printer 35 used for printing barcode on the outer wall of the solidified rock sample 18.

One side of the X-Y stepping work stand 1 is also provided with the bar code scanner 33 used for scanning the barcode on the rock sample 2.

Figure 7:
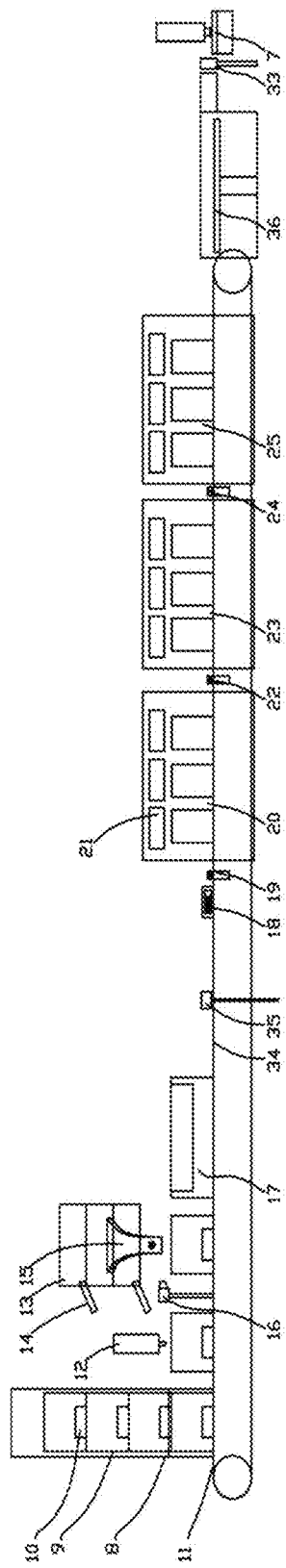
FIG. 7 is a schematic diagram of the automatic preparation and collection system in the invention.

Further preferably, as shown in FIG. 7, the buffer stocker 36 is provided in the upstream of the barcode scanner 33. The buffer stocker 36 is made of a disc type buffer stocker, which achieves buffering and supplying the rock sample 2 by rotating the disc, and the disc type buffer stocker is a commercially available product.

As provided by the preferable solution shown in FIG. 3, the coarse grinding work section 20 is configured to arrange the lower grinding apparatus 27 opposite to the upper grinding apparatus 30, and the lifting clamping head 31 between the lower grinding apparatus 27 and the upper grinding apparatus 30, and connect the lifting clamping head 31 to the lifting frame 29, and the lifting frame 29 to the lifting motor 28 through the screw nut mechanism 38, wherein the lifting motor 28 drives the lifting frame 29 up and down, so that the lifting clamping head 31 moves backwards and forwards between the lower grinding apparatus 27 and the upper grinding apparatus 30. The lifting clamping head 31 is provided with a clamping jaw that can stretch out and draw back in the radial direction, in this example, the lifting clamping head 31 is made of an electromagnetic clamping jaw, which is a purchased part and used to clamp the side walls of the solidified rock sample 18. The lower grinding apparatus 27 and the upper grinding apparatus 30 have a surface parallelism between them that meets the design requirements. This structure makes the upper and lower surfaces of the solidified rock sample 18 keep parallel.

As provided by the preferable solution shown in FIG. 4, the precision grinding work section 23 and the polishing work section 25 are configured to arrange the lifting clamping head 31 below the upper grinding apparatus 30, and connect the lifting clamping head 31 to the lifting frame 29, and the lifting frame 29 to the lifting motor 28 through the screw nut mechanism 38, wherein the lifting motor 28 drives the lifting frame 29 up and down, so that the lifting clamping head 31 moves backwards and forwards with respect to the upper grinding apparatus 30.

As provided by the preferable solution shown in FIGS. 3 and 4, one side of the coarse grinding work section 20, the precision grinding work section 23 and the polishing work section 25 is provided with a plurality of laterally-pushing cylinders 26, preferably, the piston rod end of the laterally-pushing cylinder 26 is provided with the clamping mechanical claw 261, which is an electromagnetic mechanical claw used to push the solidified rock sample 18 into the coarse grinding work section 20, the precision grinding work section 23 and the polishing work section 25, or pick out the solidified rock sample 18 from the coarse grinding work section 20, the precision grinding work section 23 or the polishing work section 25. The laterally-pushing cylinders 26 responds to each work station in the coarse grinding work section 20, the precision grinding work section 23 and the polishing work section 25.

As provided by the preferable solution shown in FIG. 2, the upstream of the coarse grinding work section, the precision grinding work section or the polishing work section is provided with detection sensors, respectively, such as the first detection sensor 19, the second detection sensor 22 and the third detection sensor 24, preferably which are a photosensor used to detect the solidified rock sample 18 passing by them, so as to push the solidified rock sample into the corresponding work station.

As provided by the preferable solution, the feeding side of the X-Y stepping work stand 1 is provided with the bar code scanner 33 used to scan the barcode on the rock sample.

Figure 12:
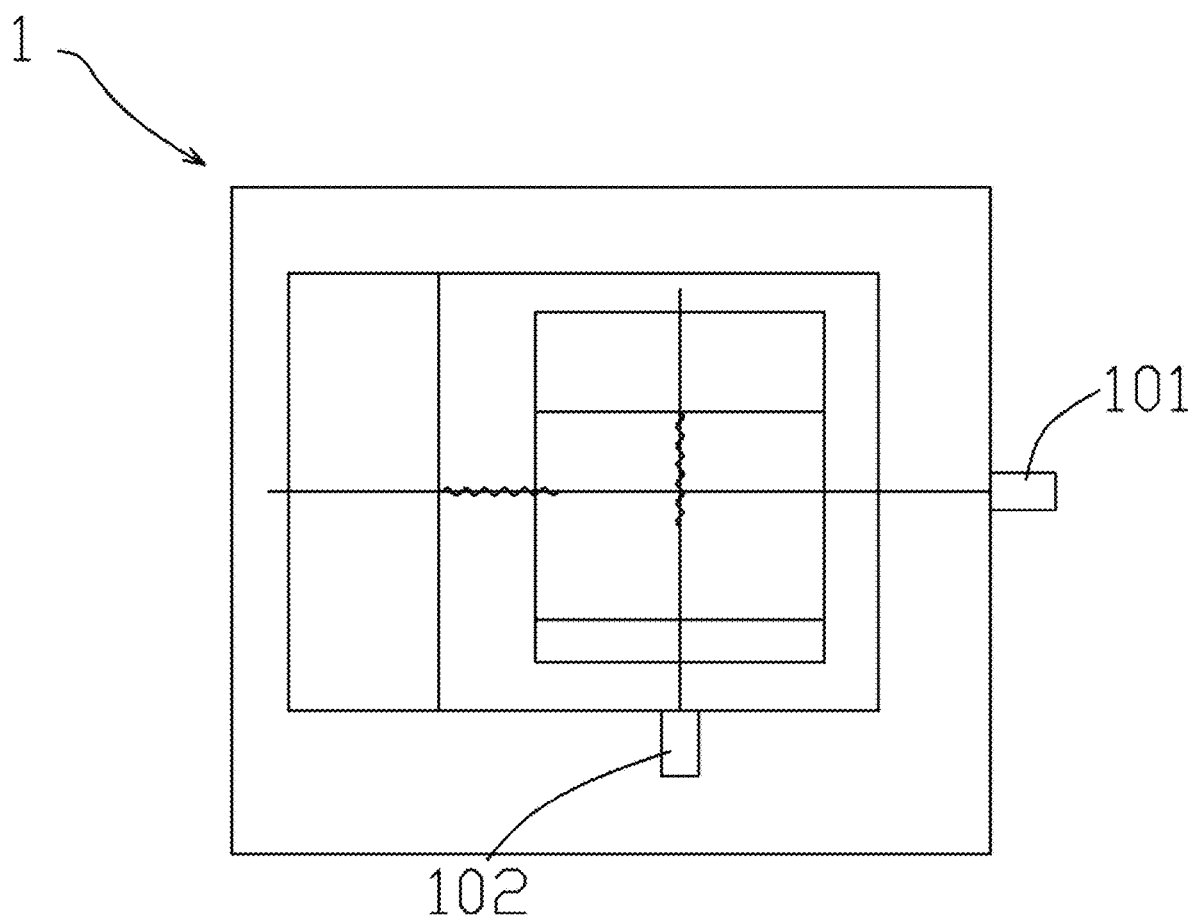
FIG. 12 is a top view of the X-Y stepping work stand in the invention.

As provided by the preferable solution shown in FIG. 12, the X-Y stepping work stand 1 is provided with the X-direction servo motor and the Y-direction servo motor, which are used to drive the work stand to move a set distance in the X-direction or the Y-direction.

Example 2

Figure 5:
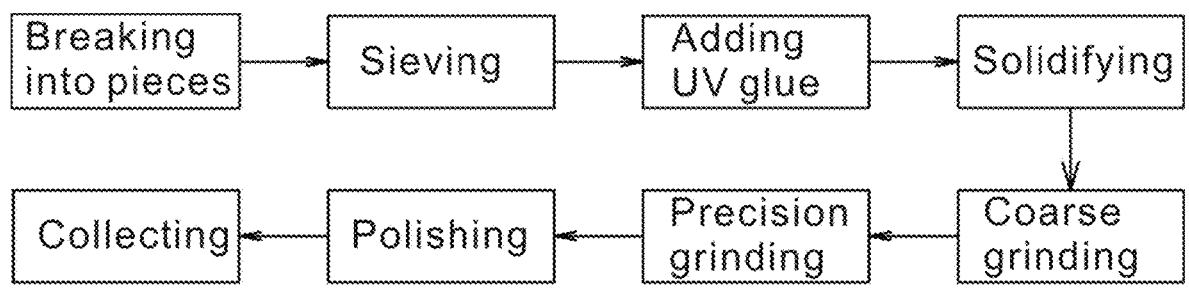
FIG. 5 is a flow chart of rock sample collection in the invention.

On the basis of Example 1 as shown in FIG. 5, an intelligent identification method adopting the intelligent quantitative microscopic identification system for whole rock polished sections mentioned above includes the following steps:

S1, breaking rocks into pieces;
S2, sieving to obtain rock samples with a particle size of 0.5~2 mm;
S3, adding UV glue into the sample vessel 9;
S4, using UV light to solidify the UV glue;
S5, coarse grinding, wherein the upper and lower end of the solidified rock sample 18 are coarsely grinded, and the surface parallelism between them meets the requirements, the coarse grinding is done with 250-mesh sandpapers;
S6, precision grinding, done with 600-mesh sandpapers;
S7, polishing, done with polishing leathers;
S8, using the X-Y stepping work stand 1 of the microscope 7 to automatically collect images of the solidified rock sample 18.

The preparation and image collection of whole rock polished sections are realized through the above steps.

Example 3

Figure 11:
FIG. 11 is a schematic diagram of images scanned by white light and spliced in the invention.

On the basis of Example 2, S7 includes the following steps: S71, fixedly installing the rock sample 2 on the X-Y stepping work stand 1 below the microscope 7, wherein, as provided by the preferable solution shown in FIG. 12, the X-Y stepping work stand 1 is provided with the X-direction servo motor 101 and the Y-direction servo motor 102, which are used to drive the work stand to move a set distance in the X-direction or the Y-direction, selecting the scanning area of rock sample 2, wherein as provided by the preferable solution, a rocking bar is installed to input X and Y-direction movement commands, so as to control the X-Y stepping work stand 1 to manually move in the X and Y directions;

S72, segmenting the scanning area, and setting the stepping length and path of the X-Y stepping work stand 1 according to the segmented scanning area, as provided by the preferable solution, manually or automatically selecting the scanning area of the rock sample 2, setting the stepping lengths of the rows and columns of the partition matrix through the computer 6 according to the visual field of a test shot so as to ensure that the segmented visual fields overlap with each other (the manual X-Y stepping work stand 1 is controlled by the rocking bar to select the scanning area of the rock sample 2, while the automagical X-Y stepping work stand 1 selects the scanning area of the rock sample 2 by inputting the scanning area in the computer 6);

S73, collecting rock sample images in different illumination modes at each stepping position, as provided by the preferable solution, arranging a light source such as the first light source 3 and the second light source 4 above the position of the fixed rock sample 2 (preferably, one of them uses a white light source, and the other uses a fluorescent light source, and the light source is provided with a plurality), when switching the light source once, sending the light source switching signal to the computer 6 once;

wherein as provided by the preferable solution, the computer 6 classifies the collected images according to the light source switching signal and the stepping signal, and the classified images are marked the same as the corresponding light source;

S74, the image collection apparatus 5 collecting images through the microscope 7 and transmitting them to the computer 6; S75, the computer splicing the collected images in sequence according to different lighting modes, with the result after being spliced shown in FIG. 11, which is a schematic diagram of the image with higher resolution spliced by the computer 6 in combination with the 1200 images which are scanned by white light and collected by the image collection apparatus 5 in this invention.

As provided by the preferable solution, the computer 6 sorts the images into the corresponding folder according to a classifying mark and order, then automatically splices the images according to the stepping sequence and the image sequence number.

As provided by the preferable solution, during the splicing process, manual accurate comparison is adopted between the first columns and between the first rows, and the computer 6 collects the overlapping parameters of the manual accurate comparison as the splicing parameters of the next columns and the next rows, and automatically completes splicing.

As provided by the preferable solution, the overlapping parameter is used as the splicing parameter of each of the later rock samples, so as to obtain a microscopic image of the organic components of the fine-grained sedimentary rock in a large visual field through the above steps.

As provided by the preferable solution, the adjacent visual fields overlap with each other by more than 10%.

Example 4

The identification method after splicing is as follows:
S01, collecting the rock sample matrix images to the computer 6 in different illumination modes, wherein as provided by the preferable solution, the illumination mode in S1 includes at least two or a combination of two or more of white light, red light, yellow light, blue light, green light and fluorescence, as provided by the preferable solution, the illumination mode in S1 includes white light and fluorescence, as provided by the preferable solution, the fluorescence is violet laser, blue violet laser or ultraviolet light, as provided by the preferable solution, the white light is a light source emitted by a high-pressure mercury lamp or a white laser light source composed of multi-color lasers, the red, yellow, blue and green light sources all pertain to laser light sources, in the collection process, in order to ensure that the image information will not be omitted when splicing them, it is necessary to ensure that the images collected at each stepping position has the edges overlapped with each other by more than 10% of the width or length, as provided by the preferable solution, in S1, when collecting, a matrix stepping stand is used to fix the rock sample, and different illumination modes are switched in each stepping, and the corresponding number of images is collected in each stepping according to the number of illumination modes;

S02, splicing matrix images, before splicing, classifying the images obtained in different lighting modes, and then querying the stepping sequence according to the number of the detected image, and automatically splicing the image according to the stepping sequence and the image sequence number, wherein during the splicing process, manual accurate comparison is adopted between the first columns and between the first rows, and the overlapping parameters of the manual accurate comparison are used as the splicing parameters of the next columns and the next rows, automatically completing splicing, preferably, the splicing parameters act as the splicing parameters in various lighting modes until the stepping parameters are re-adjusted (the stepping parameter mentioned here refers to the horizontal or vertical distance that rock sample has moved in each scanning on the work stand);

S03, tracking particulate edges on images in different illumination modes, and obtaining particulate edge-tracking images in different modes, wherein as provided by the preferable solution, in S3, how to splice images in different lighting modes and track particulate edges is to identify the boundary line in the images according to a preset threshold, and close the boundary line as a means of most approaching end so as to obtain the interface block diagram of tracking particulate edges;

S04, overlaying the particulate edge-tracking images in different modes, and keeping the edge-tracking path overlaid;

S05, classifying and extracting, wherein as provided by the preferable solution, in S5, cluster analysis is performed according to the color tone, and each cluster corresponds to the component, respectively;

wherein as provided by the preferable solution, in S6, the component corresponds to the color according to the clustering result, and each overlaid tracking path is filled with color;

S06, filling in different colors according to the classification,

S07, counting the number of color pixels and summing them.

We can quickly microscopically identify the relative content of organic components through the above steps.

Figure 8:
FIG. 8 is a schematic diagram of the whole rock polished section scanned by white light in the invention.
Figure 9:
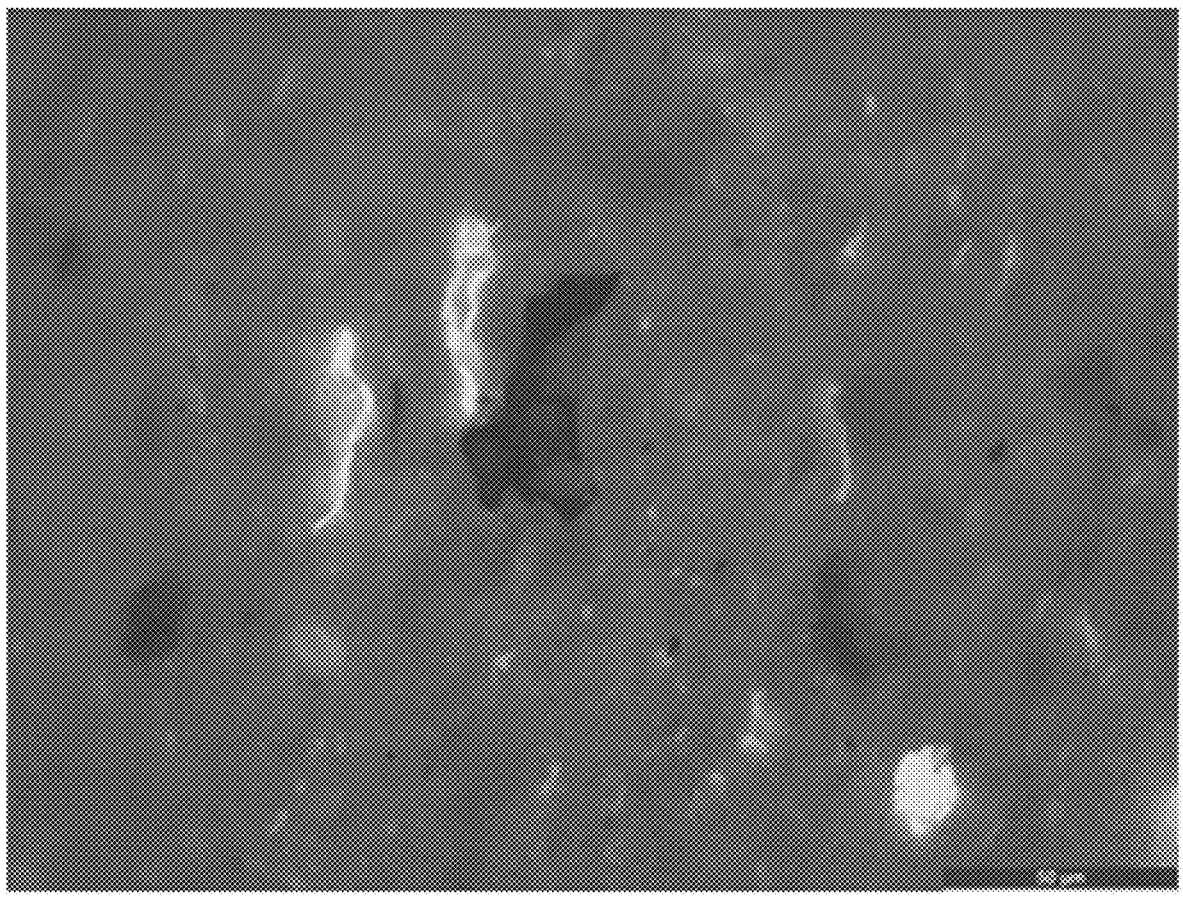
FIG. 9 is a schematic diagram of the whole rock polished section scanned by fluorescence in the invention.
Figure 10:
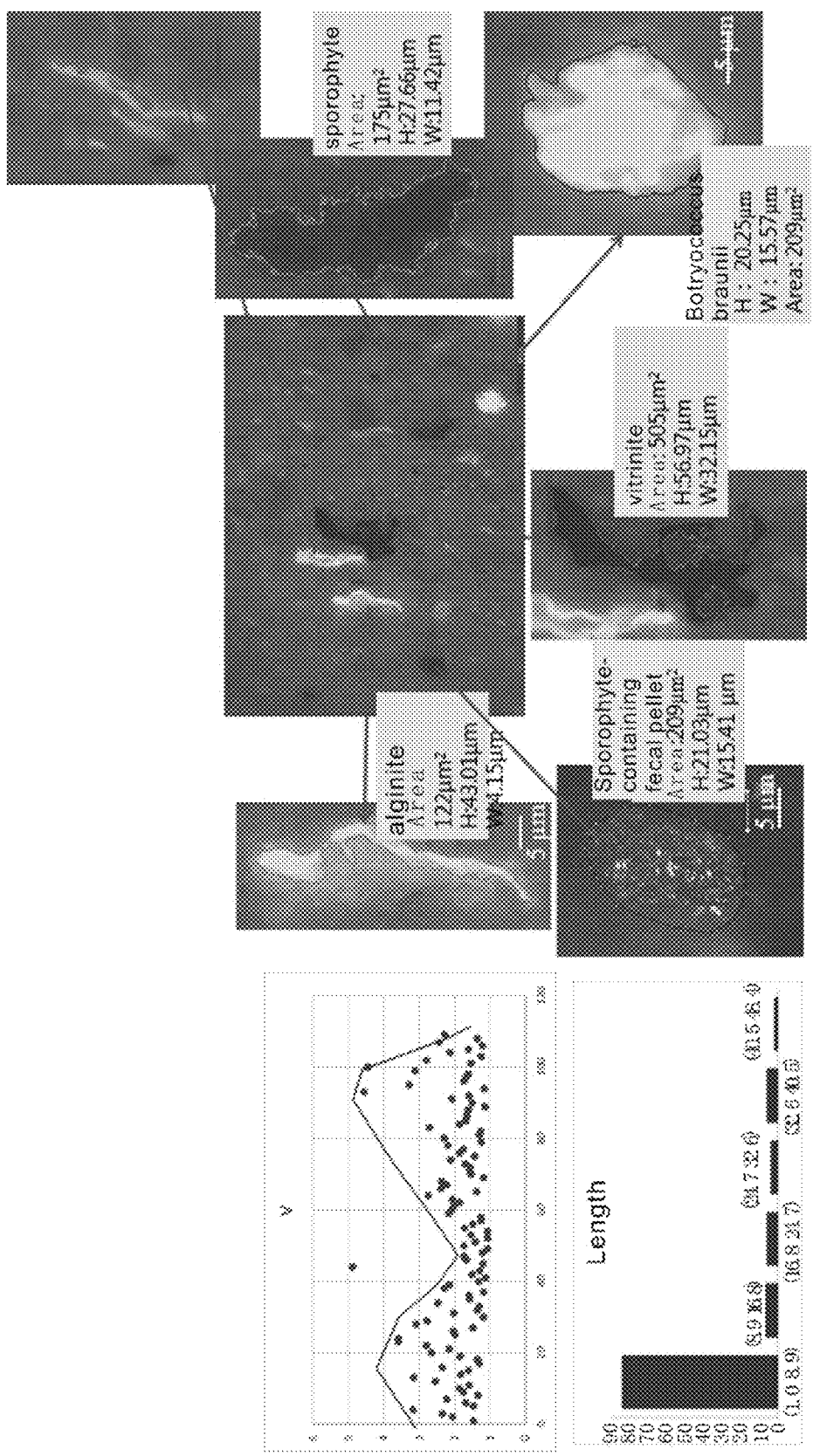
FIG. 10 is a schematic diagram of the identified components in the invention.

FIG. 8 is a schematic diagram of the whole rock polished sections scanned by the first light source 3 such as white light in the invention. FIG. 9 is a schematic diagram of the whole rock polished sections scanned by the second light source 4 such as fluorescence in the invention. The method of the invention is adopted as provide in FIGS. 8 and 9 for splicing to greatly improve the processing efficiency. FIG. 10 is a schematic diagram of identified components of the whole rock polished sections obtained in the invention. The intelligent identification and clustering statistics adopted in FIG. 10 greatly improves the efficiency of identification and statistics.

The above-mentioned embodiments are only preferable technical solutions of the invention, and should not be regarded as a limitation on the invention. The embodiments in the this application and the features in the embodiments can be combined with each other arbitrarily without conflict. The protection scope of the invention should pertain to the technical solutions described in the claims, including equivalent replacement of the technical feature in the technical solutions described in the claims. That is, equivalent replacement and improvement within this scope also fall within the protection scope of the invention.

The invention claimed is:

1. An intelligent quantitative microscopic identification system for whole rock polished sections, comprising a microscope (7), a mage collection apparatus (5) is provided with an eyepiece of said microscope (7), a light source having multiple groups of different illumination modes is provided with an objective lens (37) of said microscope (7) and a X-Y stepping working (1) stand is arranged under the objective lens of said microscope (7);

wherein said X-Y stepping work stand (1) is used to fix a rock sample (2) and drive said rock sample (2) to move step-by-step along the X and Y axes; or said X-Y stepping work stand (1) is used to fix a rock sample (2) and drive the objective lens of said microscope (7) move step-by-step along the X and Y axis;

said image collection apparatus (5) is electrically connected to computer (6);

wherein said system further including a glue-injecting apparatus (12), a vibrated delivery slideway (15), an UV solidifying tunnel (17) and a plurality of grinding working sections;

said grinding working sections includes a coarse grinding work section (20), a precision grinding work section (23) and a polishing work section (25);

said glue-injecting apparatus (12), said vibrated delivery slideway (15), said UV solidifying tunnel (17), said coarse grinding work section (20), said precision grinding work section (23) and said polishing work section (25) are arranged in sequence along the upstream and downstream of a conveyor belt (11);

said glue-injecting apparatus (12) is used to inject UV glue into a sample vessel (9);

said vibrated delivery slideway (15) is used to spread sieved rock samples on the surface of the UV glue;

said UV solidifying tunnel (17) is used to solidify the UV glue in said sample vessel (9);

said grinding section is provided with said coarse grinding work section (20), said precision grinding work section (23) and said polishing work section (25), which are used for grinding and polishing the surface of a solidified rock sample to obtain whole rock polished sections.

2. The intelligent quantitative microscopic identification system for whole rock polished sections according to claim 1, wherein said sample vessel (9) is provided with a forming ring (10), which has a transparent ring structure, and the bottom of which touches the inner bottom of said sample vessel (9) to form sealing;

a draft angle a is arranged inside said forming ring (10).

3. The intelligent quantitative microscopic identification system for whole rock polished sections according to claim 1, wherein the downstream of said UV solidifying tunnel (17) is also provided with a sampling work stand (34), one side of downstream of which is provided with a bar code printer (35);

one side of said X-Y stepping work stand (1) is also provided with a bar code scanner (33) used for scanning a barcode on said rock sample (2);

a buffer stocker (36) is provided in the upstream of said barcode scanner (33).

4. The intelligent quantitative microscopic identification system for whole rock polished sections according to claim 1, wherein said coarse grinding work section (20) is configured to arrange a lower grinding apparatus (27) opposite to an upper grinding apparatus (30), and a lifting clamping head (31) between said lower grinding apparatus (27) and said upper grinding apparatus (30), and connect said lifting clamping head (31) to a lifting frame (29), and said lifting frame (29) to a lifting motor (28) through a screw nut mechanism (38), said lifting motor (28) drives said lifting frame (29) up and down, so that said lifting clamping head (31) moves backwards and forwards between said lower grinding apparatus (27) and said upper grinding apparatus (30), said lower grinding apparatus (27) and said upper grinding apparatus (30) have a surface parallelism between them that meets design requirements.

5. The intelligent quantitative microscopic identification system for whole rock polished sections according to claim 1, wherein said precision grinding work section (23) and said polishing work section (25) are configured to arrange said lifting clamping head (31) below said upper grinding apparatus (30), and connect said lifting clamping head (31) to said lifting frame (29), and said lifting frame (29) to said lifting motor (28) through said screw nut mechanism (38), said lifting motor (28) drives said lifting frame (29) up and down, so that said lifting clamping head (31) moves backwards and forwards with respect to said upper grinding apparatus (30).

6. The intelligent quantitative microscopic identification system for whole rock polished sections according to claim 1, wherein one side of said coarse grinding work section (20), said precision grinding work section (23) and said polishing work section (25) is provided with a plurality of laterally-pushing cylinders (26), said laterally-pushing cylinder (26) is provided with a clamping mechanical claw (261) used to push the solidified rock sample (18) into said coarse grinding work section (20), said precision grinding work section (23) and said polishing work section (25), or pick out the solidified rock sample (18) from said coarse grinding work section (20), said precision grinding work section (23) or said polishing work section (25).

7. The intelligent quantitative microscopic identification system for whole rock polished sections according to claim 1, wherein the upstream of said coarse grinding work section (20), said precision grinding work section (23) or said polishing work section (25) is provided with detection sensors (19, 22, 24) respectively, which are used to detect the solidified rock sample (18) passing by them, so as to push the solidified rock sample (18) into the corresponding work station.

8. The intelligent quantitative microscopic identification system for whole rock polished sections according to claim 1, wherein the feeding side of said X-Y stepping work stand (1) is provided with a bar code scanner (33) used to scan a barcode on the rock sample.

9. The intelligent quantitative microscopic identification system for whole rock polished sections according to claim 1, wherein said X-Y stepping work stand (1) is provided with a X-direction servo motor (101) and a Y-direction servo motor (102), which are used to drive the work stand to move a set distance in the X-direction or the Y-direction.

10. An intelligent identification method adopting the intelligent quantitative microscopic identification system for whole rock polished sections mentioned above, comprising the following steps:

S1, breaking rocks into pieces;

S2, sieving to obtain rock samples with a particle size of 0.5-2 mm;

S3, adding UV glue into a sample vessel (9);

S4, using UV light to solidify the UV glue;

S5, coarse grinding, wherein the upper and lower end of a solidified rock sample (18) are coarsely grinded, and the surface parallelism between them meets requirements;

S6, precision grinding, done with 600-mesh sandpapers;

S7, polishing, done with polishing leathers;

S8, using a X-Y stepping work stand (1) of a microscope (7) to automatically collect images of said solidified rock sample (18);

so as to realize the preparation and image collection of whole rock polished sections through the above steps.

11. The intelligent identification method according to claim 10, wherein S7 includes the following steps:

S71, fixedly installing said rock sample (2) on said X-Y stepping work stand (1) below said microscope (7), said X-Y stepping work stand (1) being provided with a X-direction servo motor (101) and a Y-direction servo motor (102), which are used to drive the work stand to move a set distance in the X-direction or the Y-direction, selecting a scanning area of rock sample 2;

S72, segmenting the scanning area, and setting the stepping length and path of said X-Y stepping work stand (1) according to the segmented scanning area;

S73, collecting rock sample images in different illumination modes at each stepping position, when switching a light source once, sending the a light source switching signal to a computer (6) once, said computer (6) classifying the collected images according to the light source switching signal and a stepping signal, and the classified images being marked the same as the corresponding light source;

S74, an image collection apparatus (5) collecting images through said microscope (7) and transmitting them to said computer (6);

S75, said computer splicing the collected images in sequence according to different lighting modes, said computer (6) sorting the images into the corresponding folder according to a classifying mark and order, automatically splicing the images according to a stepping sequence and an image sequence number.

12. The intelligent identification method according to claim 11, wherein during the splicing process in S75, manual accurate comparison is adopted between first columns and between first rows, and said computer (6) collects the overlapping parameters of the manual accurate comparison as splicing parameters of the next columns and the next rows, and automatically completes splicing;

the overlapping parameter is used as the splicing parameter of each of the later rock samples;

so as to obtain a microscopic image of organic components of a fine-grained sedimentary rock in a large visual field through the above steps.

13. The intelligent identification method according to claim 11, wherein the identification method after splicing is as follows:

S01, tracking particulate edges on images in different illumination modes, and obtaining particulate edge-tracking images in different modes, how to splice images in different lighting modes and track particulate edges being to identify the boundary line in the images according to a preset threshold, and close the boundary line as a means of most approaching end so as to obtain an interface block diagram of tracking particulate edges;

S02, overlaying the particulate edge-tracking images in different modes, and keeping an edge-tracking path overlaid;

S03, classifying and extracting, cluster analysis being performed according to a color tone, and each cluster corresponding to a component, respectively;

S04, filling in different colors according to the classification;

S05, counting a number of color pixels and summing them;

so as to quickly microscopically identify the relative content of organic components through the above steps.

* * * * *